(12) United States Patent
Ancelin et al.

(10) Patent No.: US 7,394,924 B2
(45) Date of Patent: Jul. 1, 2008

(54) SCATTER CORRECTION IN SCANNING IMAGING SYSTEMS

(75) Inventors: Bruno Ancelin, Oxford (GB); Ralph Philip Highnam, Oxford (GB)

(73) Assignee: Mirada Solutions Limited, Oxford (GB)

( * ) Notice: Subject to any disclaimer, the term of this patent is extended or adjusted under 35 U.S.C. 154(b) by 680 days.

(21) Appl. No.: 10/686,382

(22) Filed: Oct. 14, 2003

(65) Prior Publication Data

US 2005/0078799 A1    Apr. 14, 2005

(51) Int. Cl.
G06K 9/00 (2006.01)
G01N 23/201 (2006.01)

(52) U.S. Cl. .......................... 382/132; 378/86
(58) Field of Classification Search ................ 382/132; 378/86–87, 98.4
See application file for complete search history.

(56) References Cited

U.S. PATENT DOCUMENTS 5,651,042 A * 7/1997 Dewaele ................. 378/62
5,883,972 A * 3/1999 Ito ............................ 382/132
6,836,570 B2 * 12/2004 Young et al. ............... 382/274
7,092,482 B2 * 8/2006 Besson ..................... 378/37

OTHER PUBLICATIONS

J. Boone et al. "Scatter/Primary in Mammography: Comprehensive Results"; Medical Physics, vol. 27, No. 10 AAPM 2000.
R. Highnam et al. "Chapter III A Model of Scattered Radiation", "Mammorgraphic Image Processing" PhD thesis; University of Oxford; 2000; Part I; "Generating $h_{int}$," pp. 57-72.
R. Highnam et al. "Computing the Scatter Component of Mammographic Images," IEEE Transactions on Medical Imaging vol. 13, No. 2, Jun. 1994, pp. 301-313.

* cited by examiner

*Primary Examiner*—Brian Werner
*Assistant Examiner*—Hadi Akhavannik
(74) *Attorney, Agent, or Firm*—Karl Bozicevic; Bozicevic, Field & Francis LLP

(57) ABSTRACT

A method of processing a radiographic image obtained with a slot-scanning radiographic system to compensate for scattering of the illuminating beam in the tissue being imaged. A conventional circularly symmetric scatter mask, for example a point spread function, is adjusted to take account of the shape of the detector and time delay integration used in the slot scanning system, the presence of an air gap between the detector and the bottom of the tissue being imaged, and the collimation of the radiation beam. The result is a sharpened and shortened point spread function.

6 Claims, 10 Drawing Sheets

Original PSF        Modulation              Slot-scan PSF

→

Normal PSF    ×          Sharpened PSF

SenoScan system, H=6cm, 300 micron resolution.

SCATTER CORRECTION IN SCANNING IMAGING SYSTEMS

TECHNICAL FIELD

The present invention relates to the processing of images obtained with scanning imaging systems, in particular to correct the images for the effects of scatter in the subject being imaged.

BACKGROUND OF THE INVENTION

Many imaging systems, for example radiography systems such as X-ray imaging systems, produce an image of a subject by passing illuminating radiation through the subject and forming on the other side an image consisting of a map of the varying degrees of attenuation of the illuminating radiation. This is the basis of the traditional X-ray image used in medical and vetinerary practice, as well as in the analysis of inanimate objects, for example in security systems. However, there are a variety of factors which tend to degrade the image produced. On the illuminating side there may be non-uniformity in the illuminating radiation, e.g. the so-called "anode-heel effect" in X-ray imaging. Degradation may also occur in the detection of the transmitted radiation. For instance in the case of a film-screen system, film saturation, film grain noise, X-ray to light conversion noise and digitiser blur for films digitised using a scanner may be present. However, a significant source of degradation is scattering of the illuminating radiation in the imaged object. This is illustrated for a typical film-screen mammography apparatus in FIG. 1 of the accompanying drawings. As illustrated an X-ray tube 1 is used to illuminate a breast 3 held between top and bottom compression plates 5, 7 spaced a distance H apart. X-rays passing through the breast impinge on the phosphor screen 9 where their energy is converted to light which is recorded on the photographic film 11. The primary X-rays passing through the breast are illustrated by the solid arrows. However, some X-rays are scattered within the breast as indicated by the dotted arrows and thus impinge on other parts of the screen-film blurring the image. The same problem arises in digital systems where the film-screen is replaced by an electronic detector (for example consisting of a combination of a fluorescent screen with a matrix of sensors sensitive to light photons). In essence the scattering means that at every pixel on the resulting image, the intensity at that pixel is due not only to the primary X-ray, but also to scattered X-rays coming from elsewhere.

A traditional way to try to reduce the effect of scatter is to use an anti-scatter grid as illustrated in FIG. 2 of the accompanying drawings. This grid 13, typically formed of lead strips, blocks X-rays coming from oblique angles (i.e. scattered X-rays) but allows the primary X-rays coming directly from the X-ray source to pass through. In order that a complete image is obtained (without unexposed areas due to the presence of the grid), the grid is moved during the exposure. While such anti-scatter grids are effective, their presence reduces the intensity of the radiation incident on the detector and so it is necessary to increase the dosage of X-ray radiation. Often it is necessary to double the dosage and this is clearly undesirable.

An approach of calculating the amount of scatter from the image itself is described in the article "*Computing the Scatter Component of Mammographic Images*", by Ralph Highnam, Michael Brady and Basil Shepstone published in IEEE Medical Image, 1994, 13, pp 301 to 313. This allows the calculation of the primary energy imparted to the detector by the subtraction of the energy due to scatter. With this approach the amount of energy reaching any pixel because of scattering is assumed to be related to, and is calculated from, the intensity of the radiation reaching the pixels in a surrounding neighbourhood. Thus the contribution due to scatter can be calculated by convoluting the intensities at the surrounding pixels with a "scatter mask". Typically the scatter mask is a cylindrically symmetric function such as that illustrated in FIG. 3. It should be noted that the scatter mask is computed for the radiography system in question, and is adjusted depending on the compressed breast thickness H. Such a scatter mask can be defined for both systems using an anti-scatter grid and systems without.

Thus the primary energy $E_p$ imparted to the detector at a pixel $(x_c, y_c)$ is $$E_p(x_c, y_c) = E(x_c, y_c) - E_s(x_c, y_c)$$

where $E_s(x_c, y_c)$ is the energy due to scatter and $E(x_c, y_c)$ is the total energy imparted to the pixel $(x_c, y_c)$. With this approach the energy due to scatter is calculated by convolving the energy values in a neighbourhood N around $(x_c, y_c)$ with a scatter mask w and multiplying by a linear scatter function s:

$$E_s(x_c, y_c) = s\left(\sum_{(x_c-x, y_c-y) \in N} E(x_c - x, y_c - y) w(x, y)\right)$$

A more recent way of minimising scattered radiation without using an anti-scatter grid is to use a so-called slot-scanning system. In such a system, rather than the whole, full-field image being obtained simultaneously, a narrow collimated beam of radiation is used together with a correspondingly narrow detector. The beam and detector are scanned across the subject. This is illustrated schematically for a mammography system in FIGS. 4 and 5. As illustrated a conventional X-ray source 1 is used but the radiation is collimated into a narrow beam by a collimator 15 and a correspondingly narrow detector 17 is used. To scan the image the collimator 15 detector 17 and X-ray source 1, which are all fixed to an arm to maintain alignment, are rotated about the rotation axis 19.

The effect of using a narrow beam and narrow detector is that the amount of scatter reaching the detector is significantly reduced. In addition the detector may be mounted spaced below the bottom compression plate 7 by a distance A. This air gap reduces scatter in the narrow dimension direction of the detector, although it increases the amount of scatter recorded in the perpendicular direction. The air gap A also magnifies the image. It is also possible to adjust the collimator 15 so as to have a different width from the detector 17. This influences the amount of scatter received on the detector. Ideally the collimator should match the detector in size, but in practice it is slightly wider. A typical detector is made of several lines of sensors, about 200 in one example or 10 in another example, and the detector moves parallel to its narrow direction by a distance of one pixel for each exposure. Thus each pixel in the final image is created by the sum of responses of a line of sensors across the detector. This is known as "time delay integration". FIG. 6 illustrates the principle in which a given pixel P at position 0 in the final image will receive signal for the whole time the detector overlaps position P, i.e. when the detector is in successive positions A B C D E and F as illustrated. For example, with a slot scanning system using a linear detector (e.g. in the SenoScan of 21 cm×1 cm) which is moving across the breast—the detector moves, an image is taken, it moves by one pixel, and another image is taken, etc.

Thus the total exposure to a pixel in the image comes from several different exposures and not in just 'one hit'. In fact in the detector a charge accumulation technique is used, so that the charge accumulated on one cell of the detector is transferred from cell to cell in the opposite direction to the motion of the detector as it moves so as to remain under the same image pixel. When it reaches the edge of the detector it is outputted as the total exposure for that image pixel.

Although the use of a slot scanning system is effective to reduce the amount of scatter in one direction, it does not eliminate scatter completely in that direction, and also gives no benefit in the perpendicular direction (the long direction of the detector). Further, as well as primary being accumulated at each pixel with the successive exposures, scatter is also accumulated. So the total exposure consists of the accumulated primary radiation and also the accumulated scatter. Even in such a slot scanning system, therefore, it would be useful to be able to reduce the degrading effect of scatter in the image. If the results of each individual exposure were known, a standard scatter function could be applied to each exposure to estimate scatter. However, in fact only the results of the accumulation of the exposures is obtained (the image), so the standard scatter mask cannot be applied.

SUMMARY OF THE INVENTION

Accordingly the present invention provides a method of processing an image obtained by a slot scanning radiographic imaging apparatus in which a collimated beam of illuminating radiation is transmitted through a subject to a detector, the method comprising the step of correcting for degradation of the image caused by scattering of illuminating radiation by applying to the image a scatter mask.

Preferably the scatter mask for the slot scanning system is obtained by adaptation of an existing full field scatter mask.

Thus another aspect of the invention provides a method of adapting a full field scatter function for a scanning, non-full field detector, such as a linear detector.

The effect of time delay integration in the detector may be allowed for, for example by summing the contributions to scatter over the width of the detector. This may be achieved by forming the scatter mask from a sum of elemental scatter masks which are adapted from a conventional scatter mask. The elemental scatter masks may be adapted from a conventional scatter mask by setting values of the conventional scatter mask to zero outside the area of illumination. Further, in summing the contributions the energy imparted to each pixel may be assumed to be the same at each detector position for that pixel.

The scatter mask may be adapted to allow for the effect on scatter of time delay integration in the detector by multiplying a full field scatter mask by a piecewise linear function, such as a sawtooth function.

The scatter mask may be adapted to allow for the effect of the distance between the detector and subject i.e. the air gap. It will be recalled that the amount of scatter, and thus the scatter mask, is dependent upon the thickness of the imaged material through which the illuminating radiation passes. A way of allowing for the air gap is effectively to assume that the imaged material extends all the way to the detector, i.e. to add the thickness of the air gap to the thickness of the imaged material in the calculation of the scatter mask.

The invention also provides image processing apparatus which operates according to the method described above, and to a complete slot scanning radiographic imaging apparatus including such an image processing apparatus. The invention may be embodied in computer software for processing images in the form of digital data set and so the invention extends to a computer program which is adapted to execute the method above on a programmed computer system.

BRIEF DESCRIPTION OF THE DRAWINGS

The invention will be further described by way of example with reference to the accompanying drawings in which.

DETAILED DESCRIPTION OF AN EMBODIMENT

An embodiment of the invention will now be described in which a scatter mask is derived which can be applied to images obtained by use of a slot scanning radiographic system such as the Fischer SenoScan. In this embodiment this will be achieved by taking a known full-field scatter mask, such as that illustrated in FIG. 3, and adapting it to take account of the differences when using slot-scanning, in particular for:

(i) the collimation of the radiation beam;
(ii) the time-delay integration; and
(iii) the air gap between the detector and the subject.

This involves calculating an elemental scatter mask appropriate for each individual exposure in the series making up the full, accumulated exposure, and using these in conjunction with an understanding of the effect of time delay integration to calculate a new scatter mask which can be applied to the obtained, accumulated image values.

(i) Radiation Beam Collimation

Figure 7:
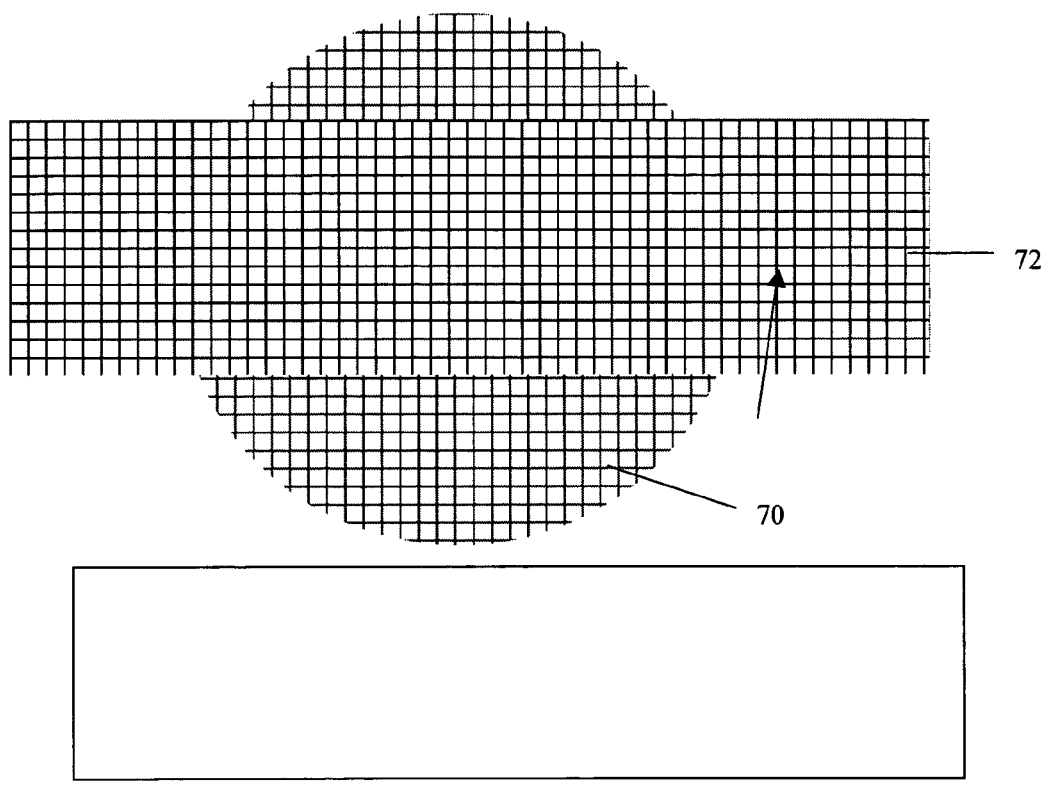
FIG. 7 schematically illustrates adaptation of a scatter mask for beam collimation.

A slot scanning system uses a linear detector and a tightly collimated X-ray beam so that scatter only comes from a restricted neighbourhood of the subject being imaged. The elemental scatter mask appropriate for each individual exposure in the series making up the full, accumulated exposure therefore needs to take account of the collimation of the radiation beam (the collimator is slightly smaller than the detector so the size of the detector does not matter in this step). In this embodiment it is assumed that the radiation beam is centred on the detector and the collimation of the beam is taken into account by setting the values of the elemental scatter masks to zero in those areas outside the collimated beam. This is illustrated schematically in FIG. 7. The circular area 70 illustrates schematically the extent of a conventional cylindrically symmetric scatter mask (typically in mammography these extend out to about 2 cm for systems using anti-scatter grids and about 4 cm for systems which do not use anti-scatter grids, though it depends on the thickness of tissue being imaged). The area of the radiation beam, however, is, by virtue of the collimation, a narrow rectangle as illustrated by grid area 72. The effect of collimation can therefore be taken into account by setting the values of the cylindrically symmetric scatter mask to 0 in the areas of the circle 70 falling outside the rectangle 72.

(ii) Time-Delay Integration

Figure 8:
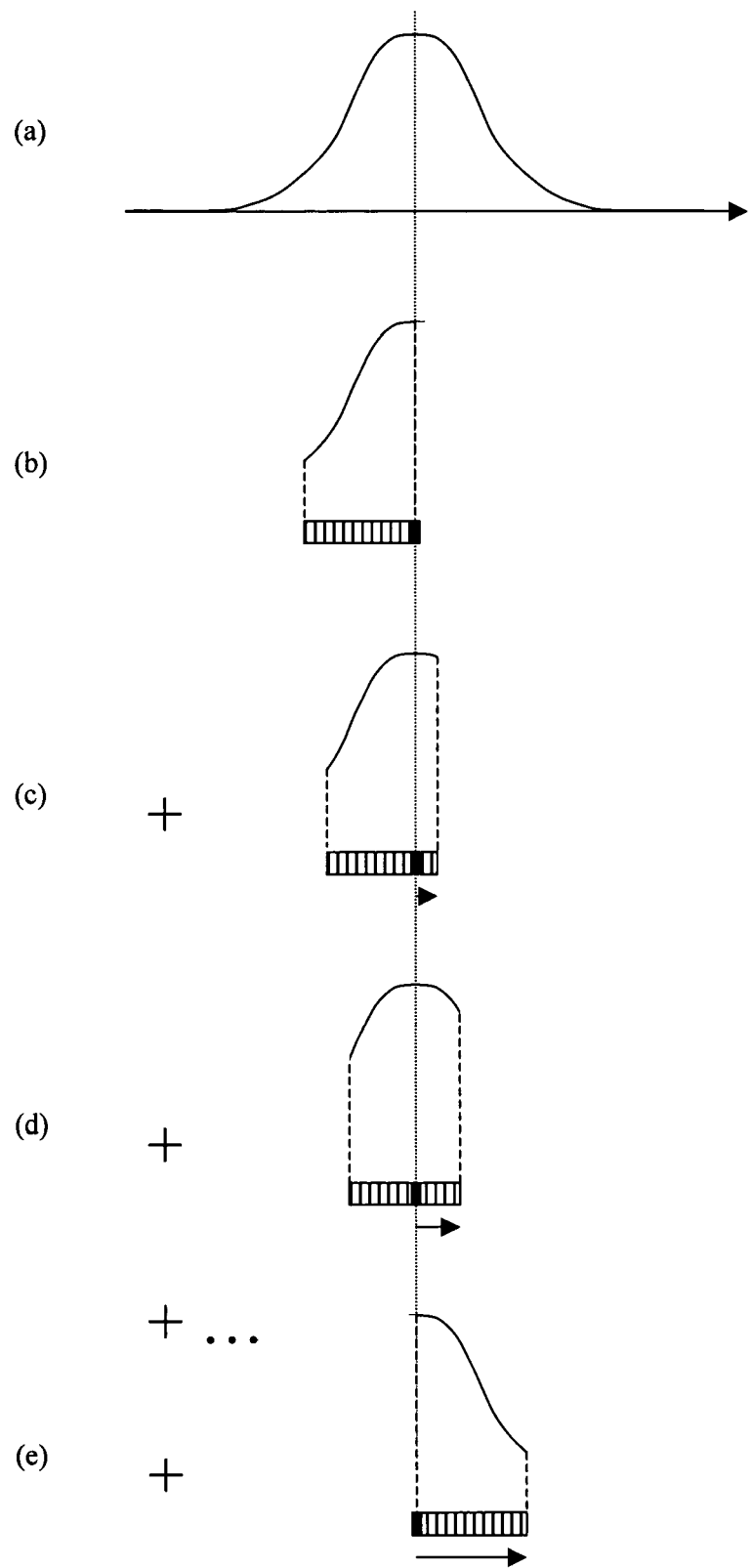
FIG. 8 schematically illustrates the scatter contributions as the detector moves.

As mentioned above each pixel in the image is subject to several exposures as the detector and beam move across the breast. Thus scattered radiation is reaching the pixel from a distance on either side of the detector approximately equal to the beam diameter. However, as the beam and detector move across the breast (effectively across the image) different elements of the mask have to be set to zero. FIG. 8(*a*) schematically shows a full scatter mask. When a pixel has only just come "into view" as in FIG. 8(*b*), it will only be receiving scatter from the illuminated half of its neighbourhood, there will be no scatter from the half of its neighbourhood which is still not illuminated, so the mask is set to zero in those areas, leaving just the left-hand half of the conventional scatter mask also cut-off at the left-hand edge of the beam. One exposure later as in FIG. 8(*c*) the elemental mask gains a little part of the right-hand half and loses part of the left. When it is in the middle it will receive scatter from both sides as shown in FIG. 8(*d*) and when it is just about to disappear as shown in FIG. 8(*e*), it will receive scatter again from only the illuminated half of its neighbourhood.

In this embodiment the effect of this is estimated as follows:

Let us denote p(dx, dy) the usual point spread function for proportion of scatter when a normal equipment is used; dx, dy are coordinates relative to the pixel of interest.

Let $\delta_{[a,b]}(x)$ be the characteristic function of [a,b] (1 over [a,b], 0 outside).

Let p'(dx, dy) be the slot-scan equivalent PSF we are trying to find.

Let s be half the width of the detector (for the purpose of this demonstration, all dimensions are given in pixels).

Generally, the scatter component of the energy at a pixel is computed by convolving the total energies (primary plus scatter) in the neighbourhood around the pixel with the point spread function in the neighbourhood around the pixel:

$$E_s = E_{ps} * p$$

The elementary contribution to scatter for each individual acquisition (i.e. for this position of the detector) would thus be:

$$E_s^{elem(i)} = E_{ps}^{elem(i)} * (p(dx, dy) \times \delta_{[-2s+i,i]}(dx))$$

The delta function having the effect of setting the mask to zero outside the collimated beam area. The total scatter contribution after the whole accumulated exposure is the sum of these elementary contributions. However $E_{ps}^{elem(i)}$ (which is the energy at each elemental exposure) is unavailable, as mentioned above. Therefore the accumulated energy read from the image ($E_{ps}^{image}$) divided by the number of lines in the detector (2s+1) is used as an estimate of $E_{ps}^{elem(i)}$. This amounts to assuming that $E_{ps}^{elem(i)}$ is slowly changing over [−s,s].

Thus:

$$E_s^{elem(i)} = \frac{E_{ps}^{image}}{2s+1} * (p(dx, dy) \times \delta_{[-2s+i,i]}(dx))$$

The total scatter energy is thus:

$$E_s^{image} = \frac{E_{ps}^{image}}{2s+1} \left( \sum_{i=-s}^{s} \delta_{[-s+i,s+i]}(dx) \right) * p(dx, dy)$$

And the new point spread function (giving scatter energy as a function of total energy) is:

$$P'(dx, dy) = \left( \frac{1}{2s+1} \times \sum_{i=-s}^{s} \delta_{[-s+i,s+i]}(dx) \right) \times p(dx, dy)$$

Figure 9:
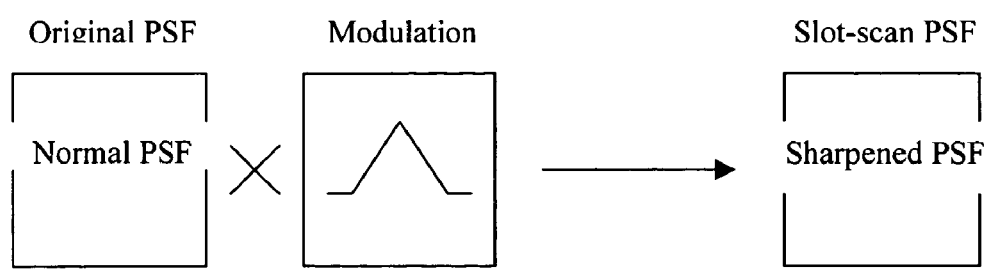
FIG. 9 schematically illustrates adaptation of a scatter mask for time delay integration.

The sum of the delta functions in parentheses is a discrete piecewise linear function (a sawtooth function) as illustrated in FIG. 9 This function is in fact a modulation function that converts the original PSF p into the new one p'. The modulation of the PSF only happens in the shorter direction of the detector. The PSF is not affected in the other direction. Representing the sawtooth function as an absolute value function of extension 4s the PSF can be written as:

$$P'(dx, dy) = \text{abs}\left( \frac{2s - dx}{2s} \right) \times \delta_{[-2s,2s]}(dx) \times p(dx, dy)$$

It was mentioned above that in certain circumstances the collimator may be set to be wider than the detector. In this case the scatter mask can be adapted to take this into account as follows.

Let c be the distance between the left side of the collimator and the left side of the detector (i.e. 2c+2s is the size of the new collimator). The scatter received for this pixel and this detector is then a fraction of p(dx,dy)*δ[−2s−c,c](dx,dy). The total is then:

$$P''(dx, dy) = \left( \frac{1}{2s+1} \right) \times \sum_{i=-s}^{s} \delta_{[-s-c+i,+s+c+i]}(dx) \times p(dx, dy)$$

Likewise for the normal case, the sum works out to be a piecewise linear function with the following segments:

0 over ]−inf,−c−2s]
linear up to 1 over [−c−2s,−c]
1 over [−c,c]
linear down to 0 over [c,c+2s]
0 on [c+2s,+int[

The scatter spatial extension of the PSF in the detector principal direction is then 4s+2c.

(iii) Air Gap

As mentioned above often in slot scanning systems the detector is mounted a certain distance A below the subject being imaged, e.g. below the bottom compression plate in a mammographic system, this spacing being known as the air gap. The air gap is useful, not only in providing magnification but also because of the use of the small sized detector, the air gap means that more scatter tends to miss the detector. Conventional circularly symmetric scatter masks such as that shown in FIG. 3 consist of values which depend on the thickness of tissue being imaged. In the case of a mammogram this is the compressed breast thickness H. In this embodiment the scatter mask values are replaced by values for a compressed breast thickness H'=H+A, i.e. the actual compressed breast thickness plus the air gap A. In effect this models the air gap as being full of breast tissue. This is an acceptable approach where no anti-scatter grid is used because the scatter mask makes no assumption about where the scattering material is located above the pixel. If an anti-scatter grid is used then the position of the scattering material is important because the grid only allows through scatter coming from a narrow range of angles and positions above the pixel. In that case the scatter mask would be recalculated to take into account the air gap.

Figure 1:
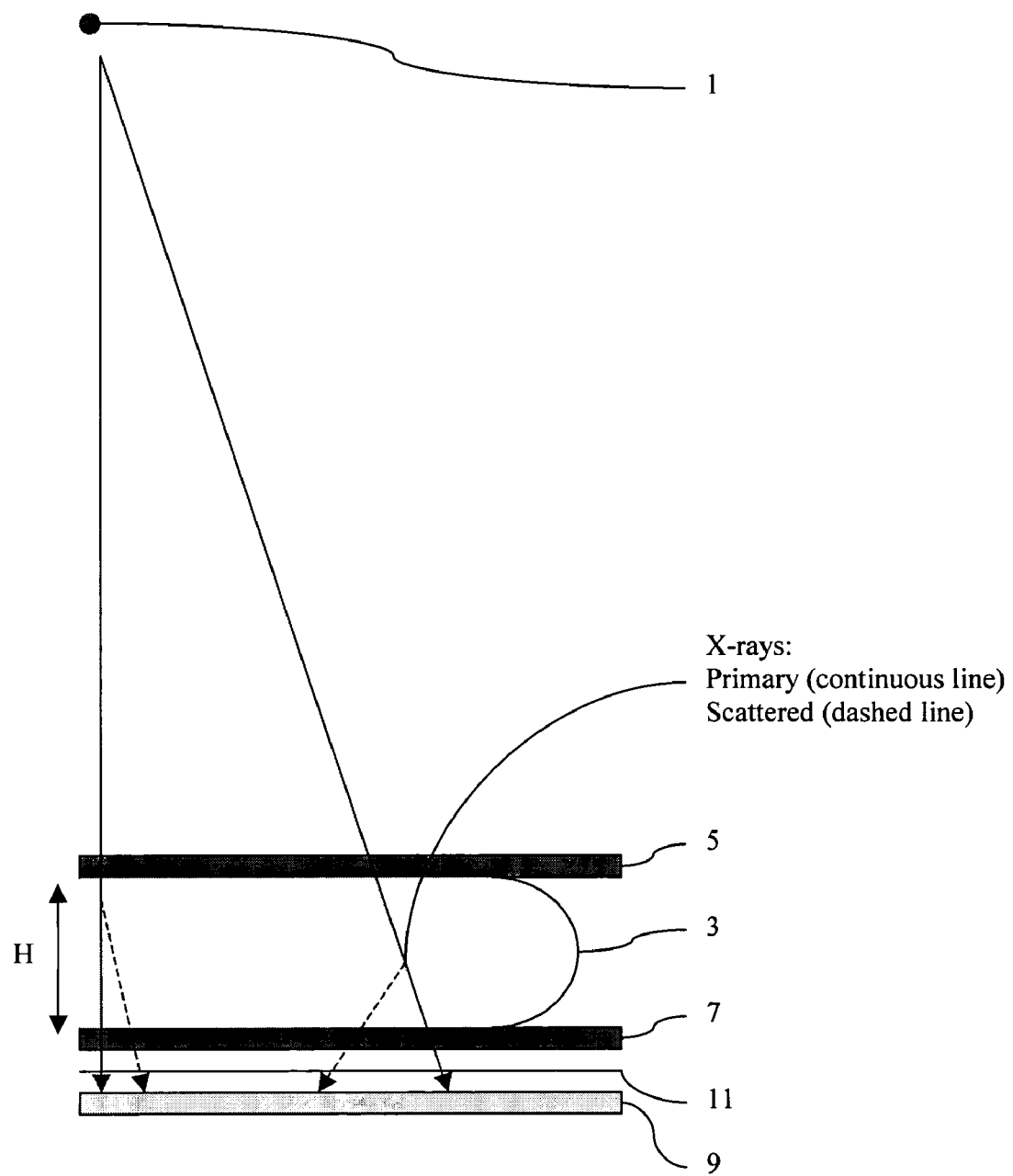
FIG. 1 is a schematic diagram of typically film-screen mammography apparatus.
Figure 2:
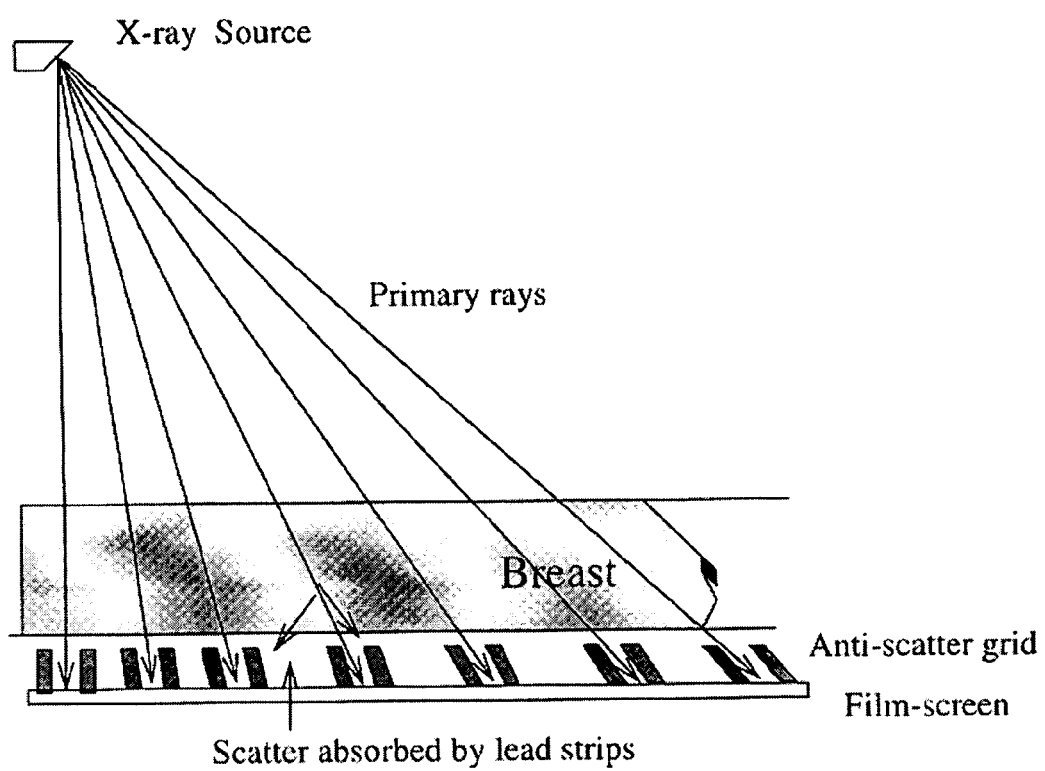
FIG. 2 is a schematic representation of such apparatus using an anti-scatter grid.
Figure 3:
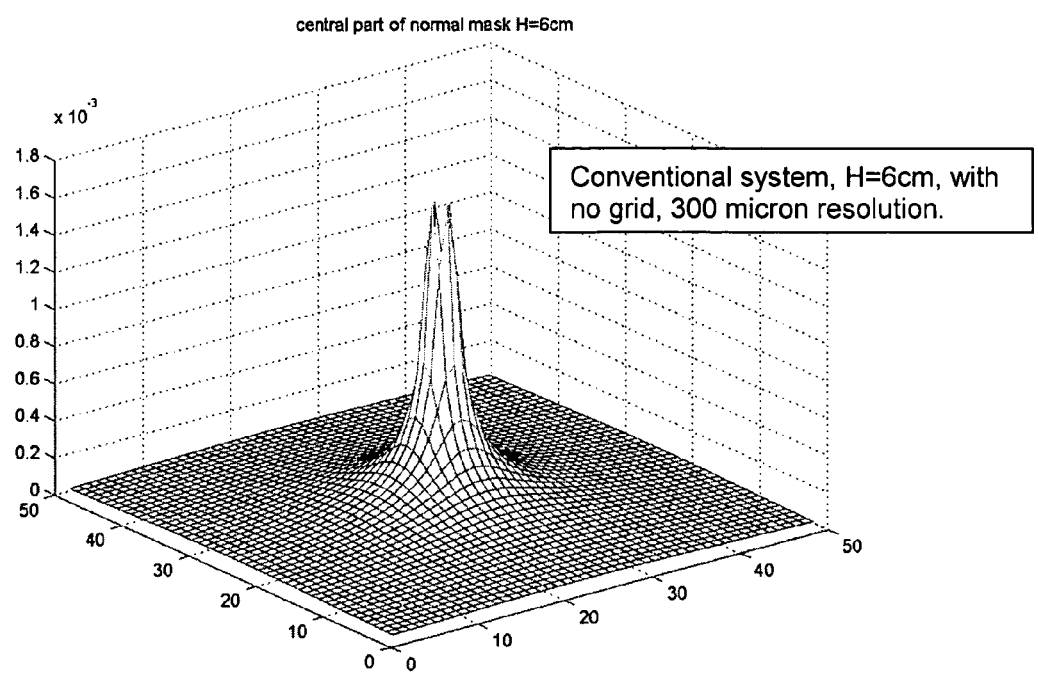
FIG. 3 illustrates a conventional scatter mask for a full-field radiographic apparatus.
Figure 4:
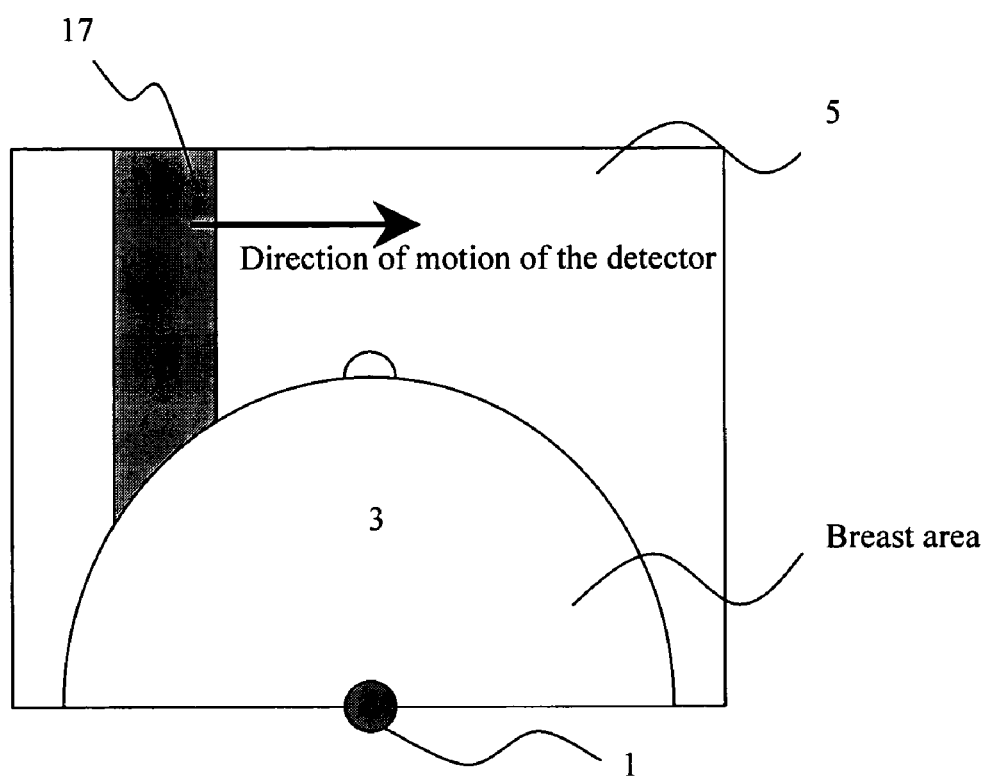
FIG. 4 is a schematic top view of a slot-scanning mammographic apparatus.
Figure 5:
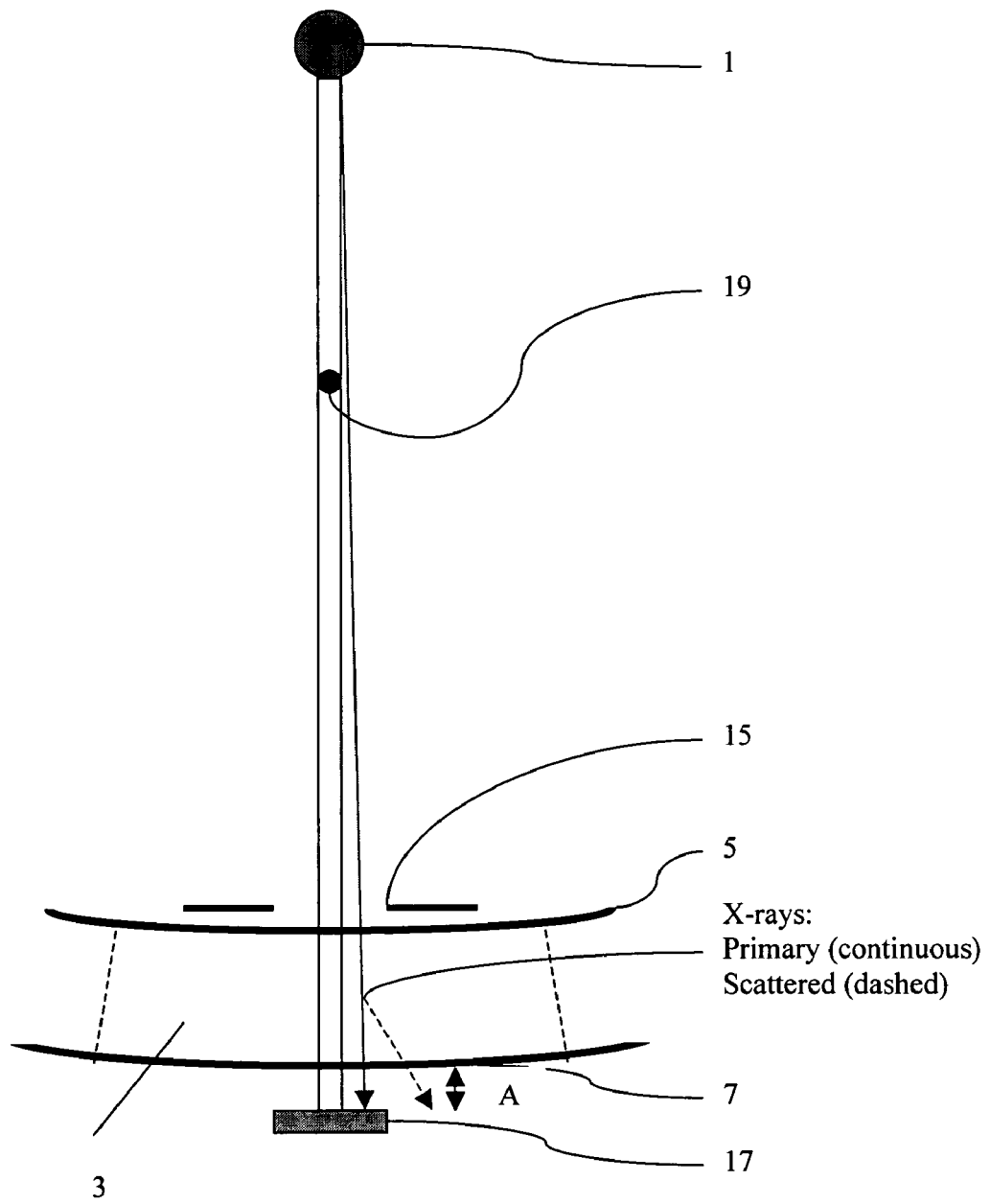
FIG. 5 is a schematic front view of the slot-scanning apparatus of FIG. 4.
Figure 6:
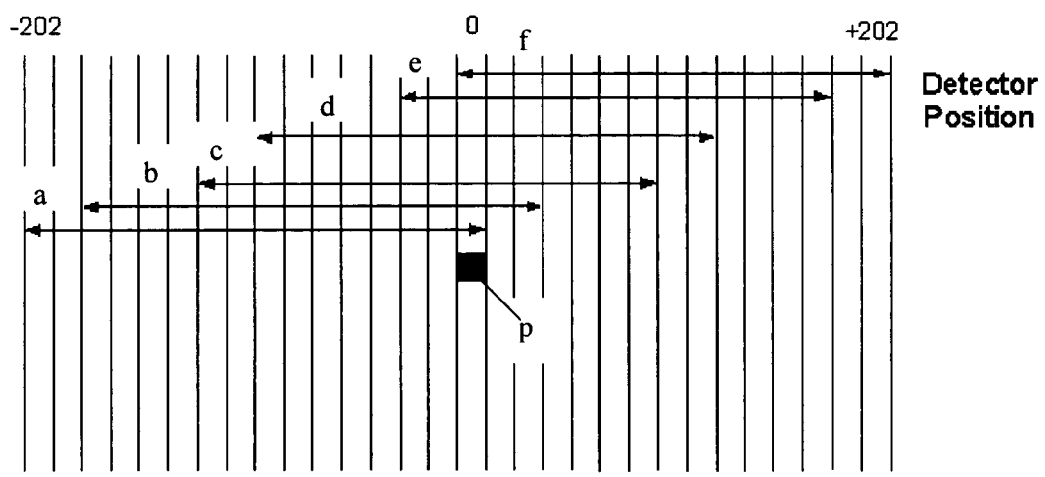
FIG. 6 illustrates the principle of time delay integration in such a slot-scanning system.
Figure 10:
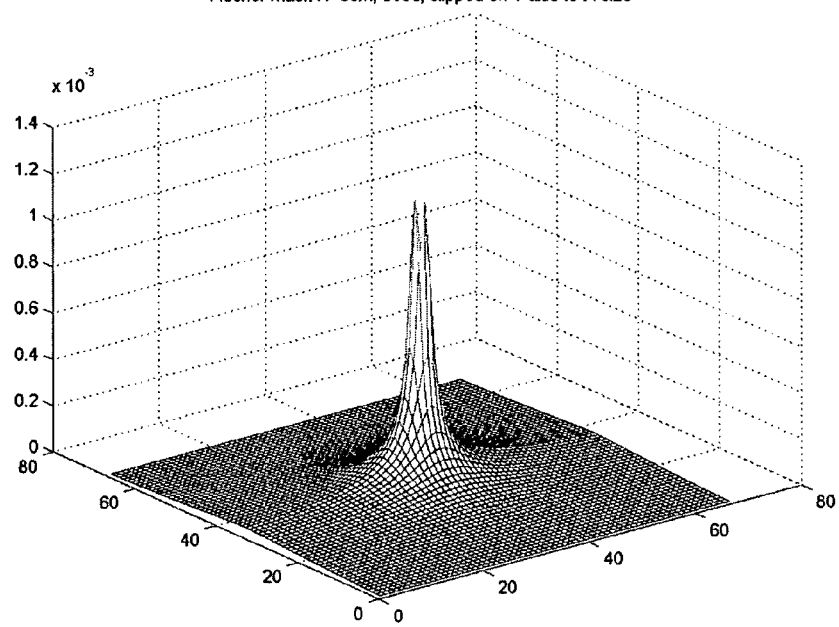
FIG. 10 illustrates a scatter mask obtained using an embodiment of the invention for a slot-scanning radiographic apparatus.

FIG. 10 illustrates the new scatter mask resulting from applying the adaptations above to the conventional psf shown in FIG. 3. It can be seen that the mask is sharpened compared to the conventional psf, and is also shortened in one direction because of the use of the narrow detector.

What is claimed is:

1. A method of processing an image obtained by a slot scanning radiographic imaging apparatus in which a collimated beam of illuminating radiation is transmitted through a subject to a detector to produce said image, the method comprising the steps of:

taking a full field scatter mask which defines the contribution of scattered radiation to the intensity of the image at a given detector position in terms of the intensity at a plurality of surrounding detector positions;

preparing an adapted scatter mask representing the sum of a plurality of elemental scatter masks, each of said plurality of elemental scatter masks corresponding to a different exposure position of said beam and detector relative to said subject, and each of said plurality of elemental scatter masks having values of the full field scatter mask set to zero outside the area of illumination to allow for an effect on scatter due to collimation of the illuminating radiation; and convolving the image produced by the detector with the adapted scatter mask to correct for degradation of the image caused by scattering of the illuminating radiation.

2. A method according to claim 1 wherein the scatter mask is adapted to allow for the effect on scatter of the distance between the detector and the subject.

3. A method according to claim 2 wherein the scatter mask is adapted to allow for the effect on scatter of the distance between the detector and the subject by assuming that the subject extends up to the detector.

4. A method according to claim 1 wherein the adapted scatter mask is prepared by multiplying a full field scatter mask by a piecewise linear function.

5. A method according to claim 4 wherein the piecewise linear function is of sawtooth shape.

6. A computer readable storage medium carrying a computer program comprising program code means for executing on a programmed computer system the method of claim 1.

* * * * *